United States Patent [19]

Sato et al.

[11] Patent Number: 4,643,813
[45] Date of Patent: Feb. 17, 1987

[54] PROCESS FOR PRODUCING ALKANESULFONIC ACIDS

[75] Inventors: Yasukazu Sato; Kenichi Matsuda; Hiromi Ozaki; Teruo Suzuka; Mamoru Yamane, all of Saitama, Japan

[73] Assignee: Nippon Mining Co., Ltd., Tokyo, Japan

[21] Appl. No.: 775,295

[22] Filed: Sep. 12, 1985

[30] Foreign Application Priority Data

Dec. 13, 1984 [JP] Japan ................................ 59-261880
Aug. 5, 1985 [JP] Japan ................................ 60-171035

[51] Int. Cl.$^4$ ................................................ C07C 3/24
[52] U.S. Cl. ................................................ 204/157.78
[58] Field of Search ..................... 260/513 R, 513 B; 204/157.78

[56] References Cited

U.S. PATENT DOCUMENTS 3,372,188 3/1968 Alston et al. ................... 204/157.78
3,956,371 5/1976 Bjellqvist ....................... 260/513 R
4,518,537 5/1985 Pistorius ....................... 204/157.78

Primary Examiner—Alan Siegel
Attorney, Agent, or Firm—Sughrue, Mion, Zinn, Macpeak & Seas

[57] ABSTRACT

A process for producing an alkanesulfonic acid is described, which comprises causing sulfur dioxide and oxygen to act on a saturated hydrocarbon under illumination with light in a substantially water-free reaction system, wherein photo-sulfoxidation of the saturated hydrocarbon is performed as a reaction mixture in the reaction system is held in contact with sodium sulfite.

14 Claims, 2 Drawing Figures

PROCESS FOR PRODUCING ALKANESULFONIC ACIDS

FIELD OF THE INVENTION

The present invention relates to a process for producing an alkanesulfonic acid and more particularly, to a process for producing an alkanesulfonic acid by causing sulfur dioxide and oxygen to act on a saturated hydrocarbon under illumination with light in a substantially water-free reaction system.

BACKGROUND OF THE INVENTION

A photo-sulfoxidation method is known in which a saturated hydrocarbon is photo-sulfoxidized with sulfur dioxide and oxygen in a substantially water-free reaction system. In this method, colored materials are deposited on the surface of a light source and will impair the light illumination to such an extent that the intended photo-sulfoxidation is considerably retarded. When certain amounts of such colored materials are deposited on the surface of the light source, the reactor must be shut down for the purpose of removing the deposit, but this is quite inefficient and makes continuous operation of the reactor impossible.

Under these circumstances, the commercial production of alkanesulfonic acids has been limited to photo-sulfoxidation in the presence of water. However, the reaction efficiency of this method is low because the water used inhibits the radical chain reaction. In addition, sulfuric acid is formed as a by-product in an amount substantially equimolar to the intended alkanesulfonic acid, and in order to separate the sulfuric acid, the water must be distilled off at from 90° to 140° C. This produces an undesired odor or color in the alkanesulfonic acid.

Even the method of photo-sulfoxidation in the presence of water is not completely free from the formation of colored materials. A method has been proposed for inhibiting the formation of such colored materials, which involves first irradiating the saturated hydrocarbon with UV light in the presence of sulfur dioxide, but in the substantial absence of oxygen, and then introducing oxygen into the irradiated saturated hydrocarbon (Japanese Patent Publication No. 28973/1972). It has also been proposed that suppression of the deposition of colored materials on the surface of a light source may be accomplished by causing a predetermined amount of nitrogen or air to flow in the area near the surface of the light source (Japanese Patent Publication No. 11740/1972).

In the first method wherein the saturated hydrocarbon is illuminated with UV light in the substantial absence of oxygen, the inadequate presence of oxygen radicals, which are an important driving force for the photo-sulfoxidation, causes the reaction to proceed at a very slow rate and makes this method unsuitable for commercial operation. In the second method wherein a stream of nitrogen or air is caused to flow in the area near the surface of the light source, contact between said surface and the reaction mixture cannot be completely prevented, and the eventual resulting fouling of the surface of the light source is still inevitable. In addition, the flowing stream of nitrogen or air drives sulfur dioxide out of the reaction mixture, so the concentration of sulfur dioxide in the reaction mixture is reduced, and thus slows down the reaction rate.

On the other hand, no proposal has been made which provides for effectively inhibiting the formation of colored materials and preventing the deposition of such materials on the surface of a light source used in the photo-sulfoxidation of saturated hydrocarbons in the substantial absence of water.

SUMMARY OF THE INVENTION

As a result of extensive studies made to solve these problems of the conventional techniques, the present inventors have now unexpectedly discovered that if the reaction mixture is brought into contact with sodium sulfite, the formation of colored materials can be inhibited without lowering the rate of photo-sulfoxidation, and that at the same time, sulfuric acid that forms in a small amount during the reaction can be removed as sodium hydrogensulfate by a solid-liquid separation technique.

The present invention has been accomplished on the basis of this discovery and has as its primary object the provision of a process for continuous production of an alkanesulfonic acid in a substantially water-free photo-sulfoxidation system of a saturated hydrocarbon without lowering the reaction rate while preventing the deposition of colored materials on the surface of a light source and effecting the removal of the by-product sulfuric acid.

This object is achieved by a process for producing an alkanesulfonic acid which comprises causing sulfur dioxide and oxygen to act on a saturated hydrocarbon under illumination with light in a substantially water-free reaction system, wherein photo-sulfoxidation of the saturated hydrocarbon is performed as a reaction mixture in the reaction system is held in contact with sodium sulfite.

In a preferred embodiment, the contact between the reaction mixture and sodium sulfite is effected either by adding sodium sulfite into the reaction mixture, or by withdrawing a portion of the reaction mixture from the system and then returning it into the system after bringing said mixture into contact with sodium sulfite.

DETAILED DESCRIPTION OF THE INVENTION

Figure 1:
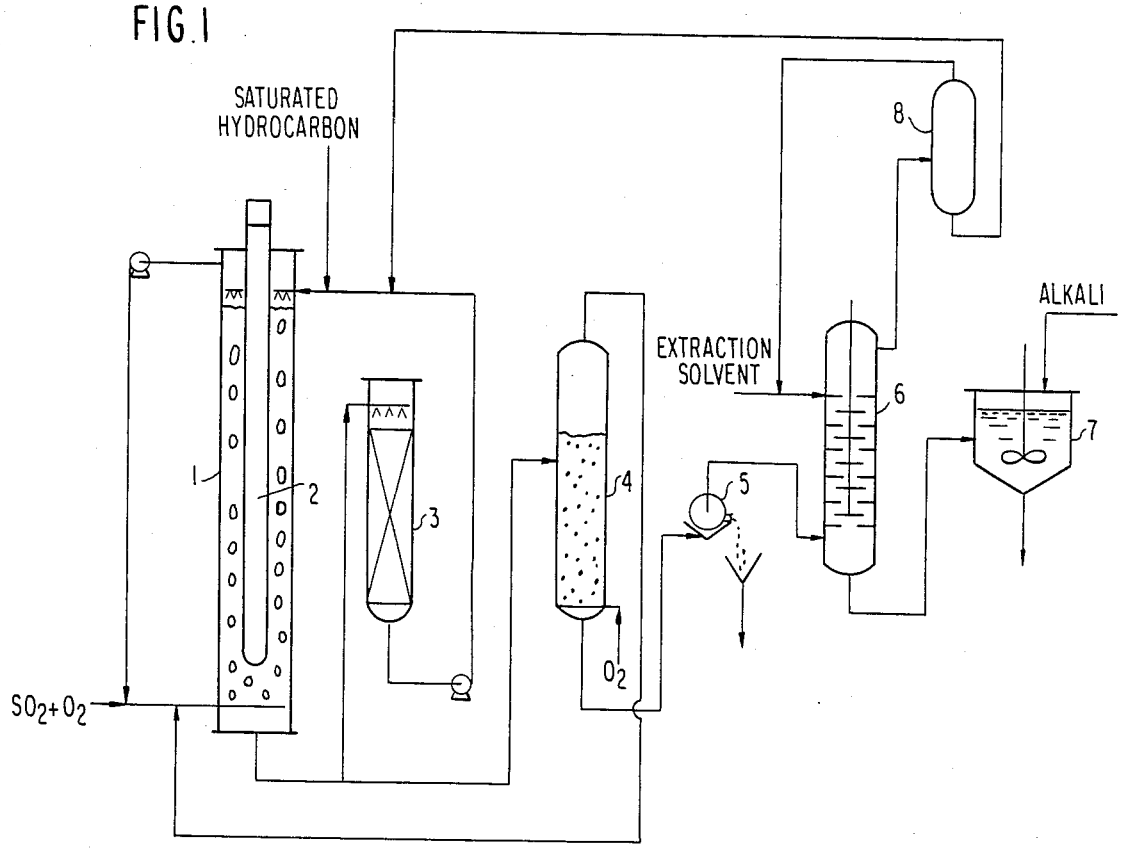
FIGS. 1 and 2 are flowcharts showing schematically two preferred embodiments of the process of the present invention.

The saturated hydrocarbon that can be used as the starting material in the process of the present invention may be any saturated hydrocarbon that will remain in a liquid state in the reaction system. If the alkanesulfonic acid produced by the process is intended for use as a starting material for the production of synthetic detergents, other surfactants, etc., normal paraffins having from 8 to 24 carbon atoms are preferred saturated hydrocarbons.

The light source used in the present invention is preferably one which is capable of radiating ultraviolet or visible light having a wavelength of from 150 nm to 500 nm and preferably from 200 nm to 400 nm.

The temperature at which the photo-sulfoxidation is performed can be appropriately selected in the range of from $-20°$ to $200°$ C. in consideration of the melting point or boiling point of the saturated hydrocarbon used. If the saturated hydrocarbon is liquid at room temperature, there is no particular need for it to be heated. The higher the reaction pressure, the greater the reaction rate, which is thus a preferred condition for purposes of the present invention. However, pressures in the range of from 0 to 50 atmospheres (gauge pressure) are sufficient for practical purposes.

Sulfur dioxide and oxygen may be used in the form of a gaseous mixture, and may be held stationary in the reactor, with any loss in $SO_2$ and $O_2$ being compensated for by supplying additional amounts. The gaseous mixture may be continuously fed into the reactor. The molar ratio of sulfur dioxide to oxygen generally ranges from 1/1 to 1,000/1, and preferably from 2/1 to 100/1.

The reactor used in the photo-sulfoxidation may be of the vertical type wherein a reaction mixture is placed around a vertical light source, or of the horizontal type wherein a horizontal light source is placed within the reaction mixture. Sulfur dioxide and oxygen or a mixture thereof is introduced into the solution of saturated hydrocarbon from the bottom of the reactor through a distributor. In a preferred embodiment, part of the gas that has contacted the solution of saturated hydrocarbon and left from the solution is recirculated into the reactor.

The sodium sulfite may be in the form of anhydrous salts or heptahydrates and other salts having water of crystalliztion, but anhydrous salts are particularly preferred because they will be produce sulfuric acid due to the presence of water of crystallization. The sodium sulfite may assume any physical form such as powder, pellets, or flakes. If the sodium sulfite is added to the reaction system either directly or in the form of a slurry, a powder is preferred, and if the sodium sulfite is packed in a column, pellets or flakes are preferred.

The sodium sulfite added to the reaction mixture is presumed to dissolve in the solution so as to decompose and otherwise eliminate any material that is responsible for the formation of undesired colored materials.

If the sodium sulfite is directly added to the reaction system, it may be added to the saturated hydrocarbon that is to be charged into the reactor; alternatively, the sodium sulfite may be directly added into the reaction mixture in the reactor. The preferred amount of sodium sulfite added ranges from 0.05 to 10 wt% based on the amount of the saturated hydrocarbon. If the sodium sulfite added in an amount of less than 0.05 wt%, it may tend to be unable to inhibit satisfactorily the deposition of colored materials on the surface of the light source, thus making it more difficult or impossible to effect prolonged continuous photo-sulfoxidation of the saturated hydrocarbon. For the purpose of ensuring prolonged inhibition of the deposition of colored materials, the amount of sodium sulfite is preferably maximized. However, no appreciable increase in the inhibitory action of sodium sulfite is obtained if it is added in an amount exceeding 10 wt%, and thus for economic reasons, using up to 10 wt% of sodium sulfite is preferred. Also, the reaction mixture in which the sodium sulfite is dispersed forms a dispersion within the reactor, but if the content of sodium sulfite is no more than 10 wt%, the decrease in the degree of conversion because of scattering of light and other deleterious factors will not be great enough to compromise the purposes of the present invention.

In an alternative method used to achieve contact between the reaction mixture and sodium sulfite, sodium sulfite is packed in a column and part of the reaction mixture is withdrawn from the reactor and caused to flow into the sodium sulfite packed column. The sodium sulfite reacts very fast with the substances that are believed to be responsible for the formation of colored materials, so contact between sodium sulfite and the reaction mixture is not a rate-limiting step for the prevention of the formation of colored materials and may be completed within a short time.

The amount of the reaction mixture to be withdrawn from the reactor depends on the reaction rate but is preferably in the range of from 0.01 to 1 vol%/sec, based on the total volume of the reaction mixture in the reactor. If the reaction mixture is withdrawn at a rate of less than 0.01 vol%/sec, the capability for effectively preventing the formation of colored materials is diminished. Withdrawing more than 1 vol%/sec of the reaction mixture is not economical since it simply requires the use of a large-power recirculating pump without achieving any further contribution to the purpose of preventing the formation of colored materials. As the reaction proceeds, sodium sulfite dissolves in the reaction mixture and comes out of the column but this gradual depletion of sodium sulfite can be compensated for by supplying an appropriate additional amount of sodium sulfite to the column.

Instead of feeding the withdrawn reaction mixture into the sodium sulfite packed column, a slurry of sodium sulfite may be added to the withdrawn reaction mixture; this method is preferred for environmental reasons, since the opening of a column required for sodium sulfite replenishment is obviated, thus eliminating the chance of dispersion of sulfur dioxide into the environment. The liquid component of the slurry may be supplied from the withdrawn reaction mixture or the solution of saturated hydrocarbon used as the starting material for the photo-sulfoxidation. The use of the reaction mixture from which sulfur dioxide has been removed as particularly preferred, since not only does this eliminate the chance of dispersion of sulfur dioxide, but also a highly concentrated slurry can be formed by utilizing the increased viscosity resulting from the inclusion of surface active components in the reaction mixture.

It generally suffices that sodium sulfite in the state of slurry is added to the reaction mixture in such an amount that said sodium sulfite dissolves away in the reaction mixture, but in practice it is very difficult to determine and control the amount of sodium sulfite to be dded. Therefore, in a preferred method, an excess amount of sodium sulfite in the state of slurry is added to the reaction mixture in the very early period of reaction, and such a reaction mixture is supplied from the bottom of a vessel having a greater cross-sectional area in the upper part than in the lower part, so that sodium sulfite is always kept to be fluidized in the lower part of the vessel with the additional amount of sodium sulfite to be supplied being varied according to the change in the level of the fluidized sodium sulfite.

As mentioned before, the intended effect of sodium sulfite can be obtained by only a short period of contact with the reaction mixture, so it is sufficient for the vessel to have a longitudinal length that ensures the laminar flow of liquid necessary for preventing the undissolved sodium sulfite from running off from the vessel.

Figure 2:
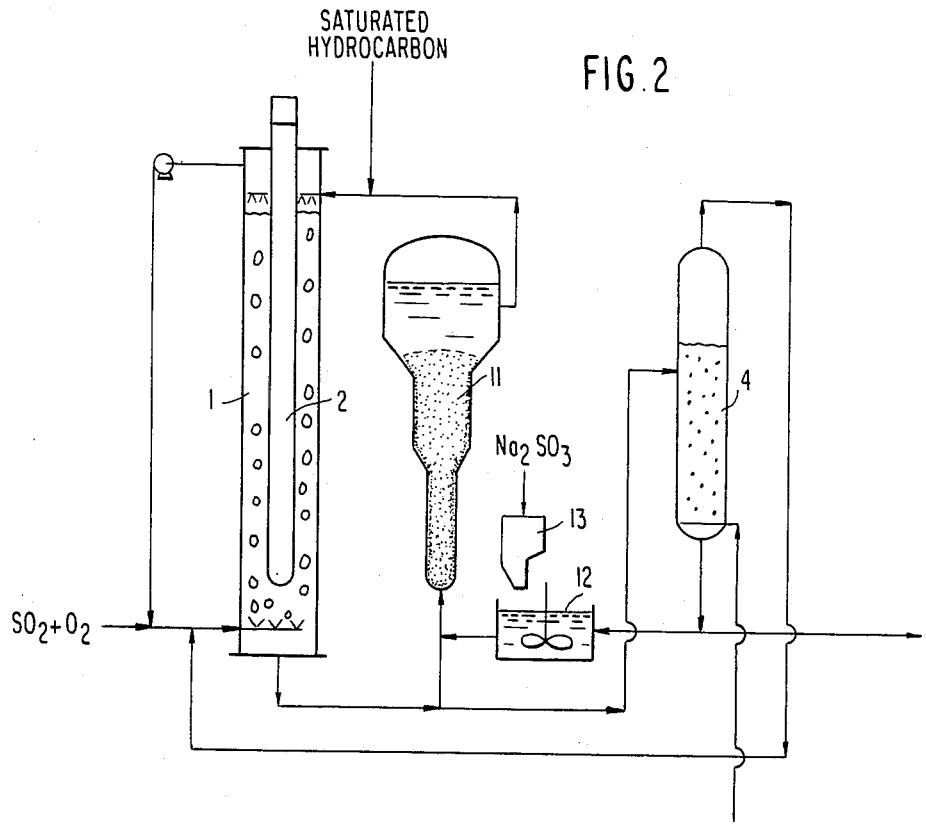

Two embodiments for implementing the process of the present invention are illustrated in FIGS. 1 and 2; FIG. 1 refers to a case wherein sodium sulfite is packed in a column, and FIG. 2 refers to a case wherein a slurry of sodium sulfite is added to the reaction mixture.

In FIG. 1, a vertical reactor generally indicated at 1 has a light source 2. A gaseous mixture of sulfur dioxide and oxygen is supplied into the reactor from the bottom, while a saturated hydrocarbon is fed from the top. The unreacted gas is withdrawn overhead from the reactor and mixed with an additional supply of sulfur dioxide and oxygen for further use in the reaction.

Part of the reaction mixture is withdrawn from the reactor 1 and is supplied into a column 3 packed with sodium sulfide. In the column 3, the reaction mixture is brought into contact with sodium sulfide, and the substances responsible for the formation of a colored material (said substances are presumed to be peroxides or their derivatives) are decomposed and removed from the reaction mixture. The reaction mixture running off from the column 3 is mixed with a fresh supply of saturated hydrocarbon and returned to the reactor 1.

The reaction time is adjusted so that the degree of conversion of the saturated hydrocarbon in the reaction mixture in the reactor lies within the range of from 0.1 to 60%, and preferably from 2 to 30%. If the degree of conversion of the saturated hydrocarbon is less than 0.1%, the economy of the operation is degraded, and if the degree of conversion of the saturated hydrocarbon is higher than 60%, alkanedisulfonic acids, or alkanetrisulfonic acids form as by-products, thus decreasing the selectivity for the intended alkanemonosulfonic acid. Since alkanemonosulfonic acid salts have properties desired for surfactants, the reaction is preferably controlled so as to minimize the formation of di- or trisulfonic acids. If the production of di- or trisulfonic acids is small, their presence in the product alkanesulfonic acid will cause no serious adverse effects on the quality of the latter.

The reaction mixture withdrawn from the reactor 1 is fed into a degassing column 4 where the reaction mixture is either bubbled with oxygen or heated or subjected to vacuum so as to remove any dissolved sulfur dioxide from the reaction mixture. The removed sulfur dioxide gas is returned for further use in the reactor 1.

As a result of degassing, crystals of sodium hydrogensulfate are precipitated in the reaction mixture. If necessary, sodium hydroxide may be added to the degassed reaction mixture so as to precipitate any residual sulfuric acid as sodium hydrogensulfate. The sodium hydrogensulfate precipitate may be separated from the reaction mixture by feeding the latter through a suitable solid-liquid separator 5 such as a filter, a sedimentation tank, or a centrifugal separator.

The reaction mixture is then introduced into an extractor 6 such as a centrifugal extractor or a rotary disk type extractor, wherein the mixture is subjected to extraction with a suitable solvent such as water, alcohol, amine, alkanolamine, or mixtures thereof. The extract containing the desired alkanesulfonic acid is introduced into a neutralizing tank 7 where it is neutralized with an alkali, for example, sodium hydroxide, potassium hydroxide or calcium hydroxide, and then is recovered as an alkanesulfonic acid salt.

The liquid raffinate coming from the extractor 6 is fed into a distillation column 8 or any other suitable means that enables the recovery of the extraction solvent. The recovered solvent is combined with the extraction solvent (not shown) recovered after the neutralization step, and the combined solvent is returned for further use in the extractor 6. The unreacted saturated hydrocarbon recovered in the distillation column 8 and any other preceding steps is recycled for further use in the reactor 1.

FIG. 2 shows an embodiment wherein a slurry of sodium sulfite is added to the reaction mixture, the components that are the same as those shown in FIG. 1 being identified by like numerals.

In FIG. 2, part of the reaction mixture withdrawn from the reactor 1 is mixed with the slurry of sodium sulfite and the resulting mixture is supplied into a vessel 11 which has a greater cross-sectional area in the upper part than in the lower part. This vessel consists of three zones; the lower zone has the smallest cross-sectional area and the upper zone has the greatest cross-sectional area with the intermediate zone having a cross-sectional area of an intermediate size. In the lower zone of the vessel 11, sodium sulfite is held at a velocity higher than the minimum fluidization velocity, and in the upper zone, the sodium sulfite is maintained at a rate lower than the terminal velocity, so that the sodium sulfite will efficiently contact the reaction mixture under fluidized conditions, and the sodium sulfite that has become smaller in particle size as a result of reaction is effectively prevented from running off from the reactor 1. The cross-sectional areas of the three zones are determined in consideration of various factors such as the particle size of the sodium sulfite used, the percent conversion of the saturated hydrocarbon in the reactor 1, the amount of the reaction mixture to be fed to the vessel 11, and the setting of the height of the slurry to be maintained during the process operation. As a result of contact between the sodium sulfite and the reaction mixture, the substances (which are believed to be peroxides or their derivatives) in the reaction mixture that are responsible for the formation of colored materials are eliminated from the reactor.

The reaction mixture that has run off from the vessel 11 is mixed with a fresh supply of saturated hydrocarbon and returned to the reactor 1.

Part of the reaction mixture withdrawn from the reactor 1 is transferred to a degassing column 4. Part of the degassed reaction mixture is sent to a slurry forming thank 12 where it is mixed under agitation with sodium sulfite being supplied from a hopper 13. The resulting slurry is added to that part of the reaction mixture which has been withdrawn from the reactor 1, and the mixture is fed into the vessel 11. The level of sodium sulfite in the vesel 11 is detected and the concentration of sodium sulfite in the slurry added or the amount of slurry added is properly adjusted to prevent the formation of colored materials or any substantial loss of the unreacted sodium sulfite from the reactor 11.

The greater part of the degassed reaction mixture is treated as in the case of the embodiment shown in FIG. 1 (the specific flowchart for this treatment is not repeated in FIG. 2).

The following examples are provided for further illustration of the claimed process, but should not be taken as limiting the invention.

EXAMPLE 1

Photo-sulfoxidation was performed with a reactor having a quartz glass protected mercury fluorescent lamp inserted through the center of a glass cylinder having an inside diameter of 50 mm and a height of 1,000 mm. The reactor was charged with 1.2 liters of normal paraffin having from 14 to 16 carbon atoms, which was subjected to photo-sulfoxidation for 1 hour with sulfur dioxide and oxygen that were introduced into the reactor from the bottom in respective hourly flow rates of 60 liters and 6 liters. After completion of the reaction, the contents of the reactor were subjected to extraction with a solvent system of water/methanol (50/50 in volume ratio) and the yield of alkanesulfonic acid was determined by the method specified in ASTM D 3049-83a, "Standard Test Method for Synthetic Anionic Ingredient by Cationic Titration". The unreacted normal paraffin that remained as the residue in the extraction step was mixed with another supply of normal paraffin having the same composition as that of the initial charge and a total of 1.2 liters of the normal paraffin was fed into the reactor. After mixing with 9 g of anhydrous sodium sulfite, the normal paraffin was subjected to another run of photo-sulfoxidation under the same conditions just described. Ten cycles of such photo-sulfoxidation were repeated, but the protective tube in the reactor will still entirely free from the deposition of colored materials, and, as is shown in Table 1 below, no drop occurred in the yield of the final product, alkanesulfonic acid.

EXAMPLE 2

The procedures of Example 1 were repeated except that the amount of anhydrous sodium sulfite was reduced to 0.9 g (0.1 wt% of normal paraffin). A small amount of a colored material was found to have been deposited on the protective tube. As shown in Table 1, the yield of alkanesulfonic acid decreased as the number of reaction runs was increased. However, the beneficial effect of the addition of sodium sulfite was nevertheless apparent in comparison with the results of Comparative Example 1.

COMPARATIVE EXAMPLE 1

Photo-sulfoxidation was performed by repeating the procedures of Example 1, except that no sodium sulfite was added. On the third run of reaction and afterward, the deposition of a colored material was observed on the protective tube. As is shown in Table 1, the yield of alkanesulfonic acid dropped drastically as the number of reaction runs increased.

TABLE 1

| Number of runs | Example 1 | Example 2 | Comparative Example 1 |
| --- | --- | --- | --- |
| 1 | 4.4 | 5.2 | 5.3 |
| 2 | 5.1 | 5.4 | 5.6 |
| 3 | 5.2 | 5.3 | 5.5 |
| 4 | 5.1 | 5.2 | 5.3 |
| 5 | 5.0 | 5.0 | 5.0 |
| 6 | 5.2 | 4.8 | 4.4 |
| 7 | 5.5 | 4.5 | 3.7 |
| 8 | 5.3 | 4.2 | 2.8 |
| 9 | 5.2 | 3.8 | 2.2 |
| 10 | 5.3 | 3.5 | 1.8 |

(The figures represent the yield of alkanesulfonic acid in terms of weight percent of withdrawn reaction mixture.)

EXAMPLE 3

Photo-sulfoxidation was performed by circulating a reaction mixture at a rate of 5 ml/sec between a reactor and a packed column. The reactor had a quartz glass protected mercury lamp inserted through the center of a glass cylinder having an inside diameter of 50 mm and a height of 1,000 mm. The column was made of glass, 200 mm high and packed with 400 g of sodium sulfite. The reactor was charged with 1.2 liters of normal paraffin having from 14 to 16 carbon atoms, which was subjected to photo-sulfoxidation for 40 minutes with sulfur dioxide and oxygen being introduced into the reactor from the bottom in respective hourly flow rates of 150 liters and 50 liters. Subsequently, the reaction mixture was withdrawn from the reactor at a rate of 30 ml/min while an equal composition as the initial charge was supplied so as to ensure continuous reaction in the reactor.

When 1.8 liters of the withdrawn reaction mixture was degassed for 60 minutes by charging oxygen at 5 ml/sec, a white powder of sodium hydrogensulfate was precipitated. Two grams of a powder of sodium hydroxide was added and after converting almost all of the residual sulfuric acid to sodium hydrogensulfate, the reaction mixture was passed through filter paper.

The filtrate was subjected to extraction with a solvent system of water/methanol (50/50 in volume ratio) and the yield of alkanesulfonic acid was determined by the method specified in ASTM D 3049-83a. The extract was substantially free from sulfuric acid. The photo-sulfoxidation was performed continuously for a period longer than 100 hours, but no deposition of any colored material occured, and as shown in Table 2, there was no drop in the yield of alkanesulfonic acid.

COMPARATIVE EXAMPLE 2

Photo-sulfoxidation was performed by repeating the procedures of Example 3, except that no column packed with sodium sulfite was used. After 1 hour, a colored material was found to have been deposited on the surface of the protective tube and the reaction mixture contained about 1 wt% of sulfuric acid which was transferred into the extract together with alkanesulfonic acid. As shown in Table 2, the yield of alkanesulfonic acid decreased with time.

EXAMPLE 2

Photo-sulfoxidation was performed by circulating a reaction mixture at a rate of 5 ml/sec between a reactor and a vessel while a slurry of 10 wt% sodium sulfite with normal paraffin (i.e., starting material) was added at a rate of 10 ml/min following the start of the withdrawal of the reaction mixture from the system. The reactor had a quartz glass protected mercury lamp inserted through the center of a glass cylinder having an inside diameter of 50 mm and a height of 1,000 mm. The vessel was stainless made and equipped with a sight glass, and had the following dimensions: ID (inside diameter) of lower section, 30.7 mm; ID of middle section, 57.2 mm; ID of upper section, 84.9 mm; height, 1,300 mm).

Normal paraffin having from 14 to 16 carbon atoms was first charged into the reactor in an amount of 1.2 liters, then charged in an amount of 3 liters into the vessel previously charged with 200 g of sodium sulfite. The charge in the reactor was subjected to photo-sulfoxidation for 140 minutes, with sulfur dioxide and oxygen being introduced into the reactor from the bottom in respective hourly flow rates of 150 liters and 50 liters. Subsequently, the reaction mixture was withdrawn from the reactor at a rate of 40 ml/min, and at the same time, the addition of a slurry of sodium sulfite was started while fresh normal paraffin was supplied at a rate of about 30 ml/min so as to maintain the liquid level constant in both the reactor and the vessel.

The withdrawn reaction mixture was filtered and the filtrate was subjected to extraction with a solvent system of water/methanol (50/50 in volume ratio) and the yield of alkanesulfonic acid was determined by the method specifid in ASTM D 3049-83a. The photo-sulfoxidation was performed continuously for a period exceeding 10 hours, but no deposition of any colored material occurred, and as shown in Table 2, there was no drop in the yield of alkanesulfonic acid. The reaction mixture withdrawn from the reactor was substantially free from unreacted sodium sulfite.

TABLE 2

| Reaction time (hr) | Example 3 | Example 4 | Comparative Example 2 |
|---|---|---|---|
| 1 | 7.5 | 5.4 | 9.7 |
| 2 | 7.8 | 5.6 | 6.9 |
| 3 | 8.1 | 5.3 | 4.9 |
| 4 | 7.7 | 5.1 | 3.0 |
| 5 | 7.0 | 5.6 | 1.9 |
| 6 | 7.2 | 5.9 | 1.3 |
| 7 | 6.8 | 5.5 | 1.0 |
| 8 | 7.4 | 5.3 | 0.8 |
| 9 | 7.1 | 5.8 | 0.6 |
| 10 | 7.3 | 5.9 | 0.5 |

(The figures represent the yield of alkanesulfonic acid in terms of weight percent of withdrawn reaction mixture.)

The process of the present invention enables continuous and efficient photo-sulfoxidation in the substantial absence of water by inhibiting the formation of colored material. In addition, the by-product sulfuric acid can be removed in the form of sodium hydrogensulfate without coloring the product alkanesulfonic acid salt.

While the invention has been described in detail and with reference to specific embodiments thereof, it will be apparent to one skilled in the art that various changes and modifications can be made therein without departing from the spirit and scope thereof.

What is claimed is:

1. A process for producing an alkanesulfonic acid which comprises causing sulfur dioxide and oxygen to act on a saturated hydrocarbon under illumination with light in a substantially water-free reaction system, wherein photo-sulfoxidation of the saturated hydrocarbon is performed as a reaction mixture in the reaction system is held in contact with sodium sulfite.

2. A process according to claim 1, wherein contact between the reaction mixture and sodium sulfite is established by adding the sodium sulfite into the reaction system.

3. A process according to claim 1, wherein contact between the reaction mixture and sodium sulfite is established by first withdrawing part of the reaction mixture from the reaction system, and then returning it to the reaction system after it has been brought into contact with sodium sulfite.

4. A process according to claim 3, wherein said contact between the withdrawn reaction mixture and sodium sulfite is made by adding a slurry of sodium sulfite into the withdrawn reaction mixture.

5. A process according to claim 3, wherein said contact between the withdrawn reaction mixture and sodium sulfite is made by adding a slurry of sodium sulfite into the withdrawn reaction mixture within a vessel having a smaller cross-sectional area in the lower section thereof than in the upper section thereof.

6. A process according to claim 4, wherein said contact between the withdrawn reaction mixture and sodium sulfite is made by adding a slurry of sodium sulfite into the withdrawn reaction mixture within the vessel having a smaller cross-sectional area in the lower section thereof than in the upper section thereof.

7. A process according to claim 1, wherein said saturated hydrocarbon is comprised of one or more normal paraffins having from 8 to 24 carbon atoms.

8. A process according to claim 1, wherein said light is ultraviolet or visible light having a wavelength of from 150 nm to 500 nm.

9. A process according to claim 1, wherein the photo-sulfoxidation is performed at a temperature in the range of from $-20°$ to $200°$ C.

10. A process according to claim 1, wherein the molar ratio of sulfur dioxide to oxygen is from 1/1 to 1,000/1.

11. A process according to claim 1, wherein the molar ratio of sulfur dioxide to oxygen is from 2/1 to 100/1.

12. A process according to claim 1, wherein the sodium sulfite is in the form of an anhydrous salt.

13. A process according to claim 2, wherein the sodium sulfite is added in a range of from 0.05 to 10 wt% based on the amount of the saturated hydrocarbon.

14. A process according to claim 3, wherein the part of the reaction mixture withdrawn from the reaction system is an amount in the range of from 0.01 to 1 vol%/sec, based on the total volume of the reaction mixture.

* * * * *